(12) United States Patent
Chung et al.

(10) Patent No.: US 11,318,180 B2
(45) Date of Patent: May 3, 2022

(54) COMPOSITION CONTAINING, AS ACTIVE INGREDIENT, GREEN TEA EXTRACT WITH INCREASED POLYSACCHARIDE CONTENT

(71) Applicant: AMOREPACIFIC CORPORATION, Seoul (KR)

(72) Inventors: Jinoh Chung, Yongin-si (KR); A Young Kim, Yongin-si (KR); Juyeon Seo, Yongin-si (KR); Bumjin Lee, Yongin-si (KR); Jeong-kee Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 16/765,823

(22) PCT Filed: Oct. 24, 2018

(86) PCT No.: PCT/KR2018/012641
§ 371 (c)(1),
(2) Date: May 20, 2020

(87) PCT Pub. No.: WO2019/098553
PCT Pub. Date: May 23, 2019

(65) Prior Publication Data
US 2020/0384058 A1 Dec. 10, 2020

(30) Foreign Application Priority Data
Nov. 20, 2017 (KR) .......................... 10-2017-0155112

(51) Int. Cl.
*A61K 36/82* (2006.01)
*A23L 33/105* (2016.01)

(52) U.S. Cl.
CPC ............ *A61K 36/82* (2013.01); *A23L 33/105* (2016.08); *A23V 2002/00* (2013.01); *A61K 2236/333* (2013.01)

(58) Field of Classification Search
None
See application file for complete search history.

(56) References Cited

U.S. PATENT DOCUMENTS

| | | | |
|---|---|---|---|
| 9,180,156 B2 | 11/2015 | Song et al. | |
| 2004/0096547 A1* | 5/2004 | Ferruzzi | A23L 5/00 426/72 |
| 2007/0020313 A1 | 1/2007 | Palat et al. | |
| 2012/0052138 A1 | 3/2012 | Park et al. | |
| 2016/0136224 A1* | 5/2016 | Cheng | A61P 3/10 424/729 |
| 2017/0007535 A1 | 1/2017 | Yoo et al. | |
| 2017/0246233 A1 | 8/2017 | Lin-Shiau et al. | |

FOREIGN PATENT DOCUMENTS

| | | |
|---|---|---|
| JP | 5342644 B2 | 8/2013 |
| KR | 10-0577677 B1 | 5/2006 |
| KR | 10-2009-0014528 A | 2/2009 |
| KR | 10-918776 B1 | 9/2009 |
| KR | 10-2010-0010132 A | 2/2010 |
| KR | 10-2010-0124519 A | 11/2010 |
| KR | 10-2015-0102326 A | 9/2015 |
| WO | 2004/112766 A1 | 12/2004 |
| WO | 2010/011020 A1 | 1/2010 |

OTHER PUBLICATIONS

Zou, X. et al. Hypoglycemic and Vasculaoprotective Effects of Tea Extract. Acta Pharmacologica Sinica 34(Suppl 1)99, Abstract S8.81 Nov. 2013. (Year: 2013).*
Xu, Y. et al. Catechins Play Key Role in Green Tea Extract Induced Postprandial Hypoglycemic Potential In Vitro. Eur Food Res Technol 237:89-99, 2013. (Year: 2013).*
Oh, J. et al. Selected Tea and Tea Pomace Extracts Inhibit Intestinal Alpha Glucosidase Activity In vitro and Postprandial Hyperglycemia In Vivo. Int J Molecular Sciences 16(4)8811-8825, 2015. (Year: 2015).*
International Search Report and Written Opinion from International Application No. PCT/KR2018/012641, dated May 10, 2019.
Xiaoling Zhou et al., "Effects of Soluble Tea Polysaccharides on Hyperglycemia in Alloxan-Diabetic Mice", Journal of Agricultural and Food Chemistry, 2007, vol. 55, pp. 5523-5528.
Yuanfeng Wang et al., "Sugar compositions, alpha-glucosidase inhibitory and amylase inhibitory activities of polysaccharides from leaves and flowers of *Camellia sinensis* obtained by different extraction methods", International Journal of Biological Macromolecules, 2010, vol. 47, pp. 534-539.

* cited by examiner

*Primary Examiner* — Ralph J Gitomer
(74) *Attorney, Agent, or Firm* — Merchant & Gould P.C.

(57) ABSTRACT

Disclosed in the present application are: a composition containing a green tea extract comprising at least one selected from the group consisting of 7 wt % or more of polysaccharides, less than 20 wt % of catechins, and 10 wt % or more of dietary fibers, relative to a total weight of the green tea extract, the composition having a use for blood glucose control; and a method for preparing the composition. The composition has not only effects of inhibiting activity of glucosidase and amylase but also effects of lowering blood glucose by inhibiting the glucose uptake in small intestinal cells.

11 Claims, 2 Drawing Sheets

COMPOSITION CONTAINING, AS ACTIVE INGREDIENT, GREEN TEA EXTRACT WITH INCREASED POLYSACCHARIDE CONTENT

CROSS-REFERENCE TO RELATED APPLICATION

This application is a National Stage Application of International Application No. PCT/KR2018/012641, filed 24 Oct. 2018, which claims benefit of Serial No. 10-2017-0155112, filed 20 Nov. 2017 in the Republic of Korea and which applications are incorporated herein by reference. To the extent appropriate, a claim of priority is made to each of the above disclosed applications.

TECHNICAL FIELD

Disclosed in the present specification are a composition which contains a green tea extract with an increased polysaccharide content as an active ingredient and has a use for regulating blood glucose, and a method for preparing the composition.

BACKGROUND ART

Blood glucose refers to glucose present in blood. The concentration of glucose in blood is maintained adequately via hormonal interactions mainly by the liver. However, with the recent economic growth and westernized eating habits in Korea, lifestyle diseases (adult diseases) such as obesity, diabetes, metabolic disorders, hypertension, heart disease, etc. are increasing due to increased blood glucose level. In particular, chronic hyperglycemia with abnormally increased blood glucose can affect other organs, too, and may lead to damage the kidney, nerves, cardiovascular system, retina, etc. and, often, unconsciousness.

Diabetes is a representative disease characterized by a high blood glucose level. It is a metabolic disease caused by insufficient secretion or improper function of insulin (DeFronzo, 1988). It is a disease characterized by various signs and symptoms associated with high blood glucose level and the presence of glucose in urine. The main cause of diabetes is obesity caused by high calorie intake, high fat intake, lack of exercise, etc. Obesity leads to insulin resistance and impaired glucose tolerance, and aggravates metabolic disorders such as hyperglycemia, hyperinsulinemia and dyslipidemia.

Dyslipidemia refers to a condition wherein total cholesterol, LDL cholesterol and triglyceride levels are increased or HDL cholesterol level is decreased in blood. LDL cholesterol is also known as bad cholesterol. Increased LDL cholesterol level leads to increased risk of heart failure, stroke, etc. HDL cholesterol is also known as good cholesterol. Increased HDL cholesterol leads to decreased risk of heart failure or stroke. Triglycerides are a type of lipids. High triglyceride level increases the risk of heart failure or stroke. Excessively increased triglycerides in blood can narrow blood vessels by adhering onto the blood vessel walls, cause thrombosis by inducing the damage of blood vessel walls, and cause vascular disorders, e.g., by inducing blood circulation from arterial vessels to peripheral vessels. This can cause arteriosclerosis, which is a risk factor of various vascular diseases, including cerebrovascular diseases such as stroke and cardiovascular diseases such as angina and myocardial infarction. As described above, chronic high blood glucose level can cause various pathological symptoms unless treated adequately. Therefore, effective management of blood glucose is necessary to prevent this.

At present, lifestyle fixation (diet therapy and exercise therapy), drug therapy, etc. are used for regulating blood glucose. However, stringent management is difficult for diet therapy and exercise therapy and the effect is also limited. Therefore, most diabetic patients depend on the correction of lifestyles as well as drugs such as insulin, insulin secretagogues, insulin sensitizers, blood glucose-lowering drugs, etc. However, there are problems in that larger quantities of drugs are required with the passage of time and they have many side effects. In order to solve these problems, research and commercialization of natural product-derived blood glucose-regulating drugs and functional foods which are nontoxic and can be used by diabetic patients for a long period of time are imminent.

REFERENCES OF RELATED ART

Patent Documents (Patent document 1) KR10-0918776 B1.
(Patent document 2) KR10-2015-0102326 A.

DISCLOSURE

Technical Problem

In an aspect, the present disclosure is directed to providing a novel use of a green tea extract with an increased polysaccharide content.

In another aspect, the present disclosure is directed to providing a composition for regulating blood glucose, which contains a green tea extract as an active ingredient.

In another aspect, the present disclosure is directed to providing a method for preparing the composition.

Technical Solution

In an aspect, the present disclosure provides a composition for regulating blood glucose, which contains a green tea extract containing one or more selected from a group consisting of 7 wt % or more of a polysaccharide, less than 20 wt % of catechin and 10 wt % or more of a dietary fiber based on the total weight of the green tea extract.

In another aspect, the present disclosure provides a method for preparing the composition, which includes: a first extraction step of adding an alcohol or an aqueous alcohol solution to green tea as a first solvent, thereby removing chlorophylls and low-molecular-weight polyphenols from the green tea; and a second extraction step of hot-water extracting water-soluble active ingredients from the extraction residue of the first extraction step.

Advantageous Effects

In an aspect, a composition which contains a green tea extract containing one or more selected from a group consisting of 7 wt % or more of a polysaccharide, less than 20 wt % of catechin and 10 wt % or more of a dietary fiber based on the total weight of the green tea extract has not only effects of inhibiting the activity of glucosidase and amylase but also effects of lowering blood glucose by inhibiting glucose uptake in small intestine cells.

BEST MODE

Hereinafter, the present disclosure is described in more detail.

In an aspect, the present disclosure provides a composition for regulating blood glucose, which contains a green tea extract containing one or more selected from a group consisting of 7 wt % or more of a polysaccharide, less than 20 wt % of catechin and 10 wt % or more of a dietary fiber based on the total weight of the green tea extract.

The green tea (*Thea sinensis*) of the present disclosure refers to an evergreen shrub or small tree belonging to the family Theaceae. In the present disclosure, both dried and undried green tea may be used without being limited to varieties or cultivation period. In addition, any part of the green tea may be used without limitation in the present disclosure. Specifically, the leaf of green tea may be used, and the green tea in the form of powder or extract may also be used.

The polysaccharide of the present disclosure collectively refers to a sugar wherein three or more monosaccharide units are bound together by glycosidic linkages. Polysaccharides may be classified into homopolysaccharides consisting of only one sugar unit and heteropolysaccharides consisting of two or more sugar units. The homopolysaccharides include neutral homopolysaccharides consisting of neutral sugar units and acidic homopolysaccharides consisting of acidic sugar units or having acidic substituents. The neutral homopolysaccharides may include starch (sugar unit: glucose), glycogen (sugar unit: glucose), chitin (sugar unit: N-acetylglucosamine), etc., and the acidic homopolysaccharides may include pectin (sugar unit: galacturonic acid), charonin sulfate (sugar unit: cellulose having a sulfate group), etc. The heteropolysaccharides include mucopolysaccharides having repeating units containing an amino sugar, glycoproteins covalently attached to proteins and having no repeating unit in the sugar moieties, glycolipids covalently attached to lipids, etc. The mucopolysaccharides may include chondroitin sulfate A (sugar units: N-acetylgalactosamine and sulfate ester of glucuronic acid), hyaluronic acid (sugar units: N-acetylglucosamine and glucuronic acid), etc. The glycoproteins may include blood group substances (sugar units: fucose, galactose, N-acetylglucosamine and N-acetylgalactosamine), serum al-acid glycoprotein (sugar units: fucose, galactose, mannose and N-acetylglucosamine), etc. The glycolipids may include O-antigen of Gram-negative bacteria (sugar units: galactose, glucose and mannose), galactan (sugar units: galactose and 3,6-anhydrogalactose), alginic acid (sugar units: mannuronic acid and guluronic acid), etc. The polysaccharides of the present disclosure may include pectin, rhamnogalacturonan I, rhamnogalacturonan II, etc., and may be polysaccharides derived from a green tea extract. The green tea extract of the present disclosure may contain the polysaccharides in an amount of 7 wt % or more, 7.1 wt % or more, 7.2 wt % or more, 7.3 wt % or more, 7.4 wt % or more, 7.5 wt % or more, 7.6 wt % or more, 7.7 wt % or more, 7.8 wt % or more, 7.9 wt % or more, 8 wt % or more, 8.1 wt % or more, 8.2 wt % or more, 8.3 wt % or more, 8.4 wt % or more, 8.5 wt % or more, 8.6 wt % or more, 8.7 wt % or more, 8.8 wt % or more, 8.9 wt % or more, 9 wt % or more, 9.1 wt % or more, 9.2 wt % or more, 9.3 wt % or more, 9.4 wt % or more, 9.5 wt % or more, 9.6 wt % or more, 9.7 wt % or more, 9.8 wt % or more or 9.9 wt % or more, specifically 9 wt % or more, more specifically 9.3 wt % or more, based on the total weight of the green tea extract.

The catechin of the present disclosure is a polyphenol which is responsible for the astringent taste of green tea. The catechin of the present disclosure may be one or more selected from a group consisting of epicatechin, epigallocatechin, epicatechin gallate and epicatechin gallate, and may be a catechin derived from a green tea extract. In addition, the green tea extract of the present disclosure may contain the catechin in an amount of less than 20 wt %, less than 18 wt %, less than 16 wt %, less than 14 wt %, less than 12 wt %, less than 10 wt %, less than 9 wt %, less than 8 wt %, less than 7.9 wt %, less than 7.8 wt %, less than 7.7 wt %, less than 7.6 wt %, less than 7.5 wt %, less than 7.4 wt %, less than 7.3 wt %, less than 7.2 wt %, less than 7.1 wt %, less than 7 wt %, less than 6.9 wt %, less than 6.8 wt %, less than 6.7 wt %, less than 6.6 wt %, less than 6.5 wt %, less than 6.4 wt %, less than 6.3 wt %, less than 6.2 wt %, less than 6.1 wt %, less than 6 wt %, less than 5.9 wt %, less than 5.8 wt %, less than 5.7 wt %, less than 5.6 wt %, less than 5.5 wt %, less than 5.4 wt %, less than 5.3 wt %, less than 5.2 wt %, less than 5.1 wt %, less than 5 wt %, less than 4.9 wt %, less than 4.8 wt %, less than 4.7 wt %, less than 4.6 wt %, less than 4.5 wt %, less than 4.4 wt %, less than 4.3 wt %, less than 4.2 wt %, less than 4.1 wt % or less than 4 wt %, specifically less than 6 wt %, more specifically less than 5.2 wt %, based on the total weight of the green tea extract.

The dietary fiber of the present disclosure is an indigestible fiber component that is not completely broken down by human digestive enzymes. It is distributed mainly in the cell wall of plant cells or the shell of plant seeds. The dietary fiber of the present disclosure may be a dietary fiber derived from a green tea extract. The green tea extract of the present disclosure may contain the dietary fiber in an amount of 10 wt % or more, 11 wt % or more, 12 wt % or more, 12.1 wt % or more, 12.2 wt % or more, 12.3 wt % or more, 12.4 wt % or more, 12.5 wt % or more, 12.6 wt % or more, 12.7 wt % or more, 12.8 wt % or more, 12.9 wt % or more, 13 wt % or more, 13.1 wt % or more, 13.2 wt % or more, 13.3 wt % or more, 13.4 wt % or more, 13.5 wt % or more, 13.6 wt % or more, 13.7 wt % or more, 13.8 wt % or more, 13.9 wt % or more, 14 wt % or more, 14.1 wt % or more, 14.2 wt % or more, 14.3 wt % or more, 14.4 wt % or more, 14.5 wt % or more, 14.6 wt % or more, 14.7 wt % or more, 14.8 wt % or more, 14.9 wt % or more, 15 wt % or more, 15.1 wt % or more, 15.2 wt % or more, 15.3 wt % or more, 15.4 wt % or more or 15.5 wt % or more, specifically 13 wt % or more, more specifically 13.6 wt % or more, based on the total weight of the green tea extract.

The monosaccharide of the present disclosure refers to a basic sugar unit of carbohydrates obtained when a polysaccharide is hydrolyzed with an acid or an enzyme, and includes glucose, fructose, galactose, mannose, ribose, etc. The monosaccharide of the present disclosure may be glucose or fructose, and may be a monosaccharide derived from a green tea extract. The disaccharide of the present disclosure refers to a substance consisting of two monosaccharide molecules, and includes sucrose formed from glucose and fructose, maltose formed from two molecules of glucose, lactose formed from glucose and galactose, etc. The disaccharide of the present disclosure may be sucrose, and may be a disaccharide derived from a green tea extract. The green tea extract of the present disclosure may contain the monosaccharide and the disaccharide in an amount of less than 7 wt %, less than 6.9 wt %, less than 6.8 wt %, less than 6.7 wt %, less than 6.6 wt %, less than 6.5 wt %, less than 6.4 wt %, less than 6.3 wt %, less than 6.2 wt %, less than 6.1 wt %, less than 6 wt %, less than 5.9 wt %, less than 5.8 wt %, less than 5.7 wt % or less than 5.6 wt %, specifically less than 6 wt %, more specifically less than 5.9 wt %, based on the total weight of the green tea extract.

The green tea extract of the present disclosure may be prepared by any method without limitation as long as a green tea extract containing 7 wt % or more of a polysaccharide, less than 20 wt % of catechin and 10 wt % or more of a dietary fiber, based on the total weight of the green tea extract, can be prepared.

According to examples of the present disclosure, a green tea extract prepared by extracting green tea firstly to remove chlorophylls and low-molecular-weight polyphenols and then hot-water extracting the resulting extraction residue secondly (Example 1) and a green tea extract prepared by precipitating the hot-water extract with an aqueous ethanol solution (Example 2) showed higher polysaccharide and dietary fiber contents, very low catechin content and lower monosaccharide and disaccharide (glucose, fructose and sucrose) contents as compared to a green tea extract prepared by filtering and drying an extract without the chlorophylls low-molecular-weight polyphenols being removed (Comparative Example) (Test Example 1 and Table 4).

The composition of the present disclosure may lower blood glucose. In addition, the composition of the present disclosure may inhibit carbohydrate digestion and glucose uptake in small intestine cells.

The composition of the present disclosure may lower blood glucose by inhibiting carbohydrate digestion. In the present disclosure, the digestion means a process where high-molecular-weight substances ingested from outside are broken down to absorbable low-molecular-weight substances in the body of an animal. The high-molecular-weight substances may be carbohydrates, and the inhibition of the digestion may mean the inhibition of the breakdown of high-molecular-weight substances to low-molecular-weight substances. In the present disclosure, the inhibition of carbohydrate digestion may be achieved by inhibiting the activity of a carbohydrate-digesting enzyme, and the carbohydrate-digesting enzyme may be amylase, glucosidase, dextrinase, lactase, sucrase or maltase, specifically glucosidase or amylase, more specifically α-glucosidase or α-amylase. According to examples of the present disclosure, the green tea extracts prepared according to the present disclosure (Examples 1 and 2) were found to have effects of inhibiting α-glucosidase and α-amylase activity in a concentration-dependent manner. Particularly, it was confirmed that a composition containing the green tea extract of the present disclosure exhibits excellent effect of lowering blood glucose since it showed superior effect of inhibiting α-amylase activity as compared to the green tea extract of Comparative Example (Test Examples 2 and 3, Tables 5 and 6, and FIG. 1).

In addition, the composition of the present disclosure may lower blood glucose by inhibiting glucose uptake in in small intestine cells. Carbohydrates are present in the form of monosaccharides such as glucose in the cavity of the small intestine due to digestion. In the present disclosure, the glucose uptake may mean the absorption of glucose into the villi of the mucous membrane of the small intestine, and the inhibition of glucose uptake may mean the inhibition of glucose present in the cavity of the small intestine into the villi of the mucous membrane of the small intestine. According to examples of the present disclosure, it was confirmed that the green tea extracts prepared according to the present disclosure (Examples 1 and 2) have an effect of inhibiting glucose uptake in small intestine cells comparably to a guava extract as a positive control group and have a better effect of inhibiting glucose uptake than the green tea extract of Comparative Example (Test Example 4, Table 8 and FIG. 3). Although the green tea extract of Comparative Example has an effect of inhibiting carbohydrate digestion by inhibiting the activity of carbohydrate-digesting enzymes, a sufficient blood glucose-lowering effect cannot be expected because the effect of inhibiting the absorption of glucose existing in the small intestine into small intestine cells is insignificant. In contrast, it was confirmed that the green tea extracts of Examples 1 and 2 of the present disclosure exhibit superior blood glucose-lowering effect by effectively inhibiting carbohydrate digestion and effectively inhibiting glucose uptake by small intestine cells.

The green tea extract of the present disclosure may be a hot-water extract obtained by hot-water extracting an extraction residue of an extract obtained by adding an alcohol or an aqueous alcohol solution to green tea as a first solvent. In addition, the green tea extract of the present disclosure may be an alcohol or aqueous alcohol solution precipitate of the hot-water extract.

The extraction residue may be one with chlorophylls and low-molecular-weight polyphenols removed.

The hot-water extraction may be for extracting water-soluble active ingredients from the extraction residue with the chlorophylls and the polyphenols removed, and the hot-water may be performed at 70-95° C. for 1-5 hours.

The precipitation using an alcohol or an aqueous alcohol solution may be performed by slowly adding an alcohol or an aqueous alcohol solution to the hot-water extract or a filtrate of the hot-water extract. The alcohol or the aqueous alcohol solution may be added with a content of 4-10 equivalents with respect to the content of the extract or the filtrate.

The alcohol or the aqueous alcohol solution may be a $C_1$-$C_5$ lower alcohol including methanol, ethanol, butanol, propanol, isopropanol, etc. or an aqueous alcohol solution thereof, or a mixture solvent with a polar solvent such as ethyl acetate, a nonpolar solvent such hexane or methylene chloride or an organic solvent. Specifically, the first solvent may be 10-90% (v/v) ethanol, more specifically 70% (v/v) ethanol. In addition, the alcohol or aqueous alcohol solution for the precipitation may be 10-99% (v/v) ethanol, more specifically 70-95% (v/v) ethanol, further more specifically 95% (v/v) ethanol.

The composition of the present disclosure may contain the green tea extract in an amount of 0.0001-99 wt %, specifically 0.1-99 wt %, more specifically 1-50 wt %, based on the total weight of the composition.

In another aspect, the present disclosure may relate to a method for regulating blood glucose, which includes administering a green tea extract containing one or more selected from a group consisting of 7 wt % or more of a polysaccharide, less than 20 wt % of catechin and 10 wt % or more of a dietary fiber based on the total weight of the green tea extract to a subject in need of blood glucose regulation. In another aspect of the present disclosure, the method may carried out according to an administration method and an administration dosage described in the present specification.

In another aspect, the present disclosure may relate to a use of a green tea extract containing one or more selected from a group consisting of 7 wt % or more of a polysaccharide, less than 20 wt % of catechin and 10 wt % or more of a dietary fiber based on the total weight of the green tea extract for preparing a pharmaceutical composition for regulating blood glucose.

In another aspect, the present disclosure may relate to a use of a green tea extract containing one or more selected from a group consisting of 7 wt % or more of a polysaccharide, less than 20 wt % of catechin and 10 wt % or more of a dietary fiber based on the total weight of the green tea extract for preparing a food composition for regulating blood glucose.

In another aspect, the present disclosure may relate to a use of a green tea extract for regulating blood glucose, wherein the green tea extract contains containing one or more selected from a group consisting of 7 wt % or more of a polysaccharide, less than 20 wt % of catechin and 10 wt % or more of a dietary fiber based on the total weight of the green tea extract.

In another aspect, the present disclosure may relate to a use of a green tea extract containing one or more selected from a group consisting of 7 wt % or more of a polysaccharide, less than 20 wt % of catechin and 10 wt % or more of a dietary fiber based on the total weight of the green tea extract for regulating blood glucose.

The composition may be a pharmaceutical composition or a food composition.

The pharmaceutical composition may be prepared into a solid, semisolid or liquid formulation for oral administration by adding a commonly used organic or inorganic carrier to the active ingredient.

Formulations for oral administration may include a tablet, a pill, a granule, a soft or hard capsule, a powder, a fine granule, a dust, an emulsion, a syrup, a pellet, etc. The formulation of the present disclosure may be prepared easily according to a common method, and a surfactant, an excipient, a colorant, a flavor, a preservative, a stabilizer, a buffer, a suspending agent or other commonly used adjuvants may be used appropriately.

The pharmaceutical composition according to the present disclosure may be usefully used for treating and preventing a disease related with blood glucose, specifically a disease caused by increased blood glucose, since it has a superior effect of regulating blood glucose, specifically lowering blood glucose. The disease related with blood glucose includes obesity, diabetes, a diabetic complication, fatty liver, hypertension, peripheral vascular disease, dyslipidemia, insulin resistance, cardiovascular disease, arteriosclerosis, metabolic syndrome, hyperglycemia, hyperlipidemia, carbohydrate metabolism disorder, etc., although not being limited thereto.

The pharmaceutical composition may be administered orally, rectally, topically, transdermally, intravenously, intramuscularly, intraperitoneally, subcutaneously, etc.

The administration dosage of the active ingredient will vary depending on the age, sex and body weight of a subject to be treated, the particular disease or pathological condition to be treated, the severity of the disease or pathological condition, administration route and the discretion of a diagnoser. The determination of the administration dosage based on these factors is within the level of those skilled in the art. A general administration dosage is 0.001-2000 mg/kg/day, specifically 0.5-1500 mg/kg/day.

The food composition may be a health food composition and may be prepared adequately according to a common method by adding the green tea extract of the present disclosure either alone or in combination with other foods or food ingredients.

The health food is not specially limited in type. Examples of the food to which the green tea extract may be added include meat, sausage, bread, chocolate, candies, snack, confectionery, pizza, ramen, other noodles, gums, dairy products including ice creams, various soups, beverages, tea, drinks, alcoholic beverages, multivitamins, etc. All health foods in ordinary meanings are included.

A health drink composition of the present disclosure may further contain various flavors or natural carbohydrates as additional ingredients like common beverages. The natural carbohydrate may be a monosaccharide such as glucose and fructose, a disaccharide such as maltose and sucrose, a polysaccharide such as dextrin and cyclodextrin, or a sugar alcohol such as xylitol, sorbitol, erythritol, etc. As a sweetener, a natural sweetener such as thaumatin or stevia extract, or a synthetic sweetener such as saccharin or aspartame may be used. The proportion of the natural carbohydrate may be 0.01-0.04 wt %, specifically 0.02-0.03 wt %, based on the total weight of the composition of the present disclosure.

In addition, the health food of the present disclosure may contain various nutrients, vitamins, electrolytes, flavors, colorants, pectic acid and its salts, alginic acid and its salts, organic acids, protective colloidal thickeners, pH control agents, stabilizers, antiseptics, glycerin, alcohols, carbonating agents used in carbonated drinks, etc. In addition, it may contain a pulp for preparing natural fruit juice, fruit juice beverages and vegetable beverages. These ingredients may be used independently or in combination. The proportion of these additives may be 0.01-0.1 wt % based on the total weight of the composition of the present disclosure.

In another aspect, the present disclosure provides a method for preparing the composition, which includes: a first extraction step of adding an alcohol or an aqueous alcohol solution to green tea as a first solvent, thereby removing chlorophylls and low-molecular-weight polyphenols from the green tea; and a second extraction step of hot-water extracting water-soluble active ingredients from the extraction residue of the first extraction step. The preparation method may further include a precipitation step of precipitating the hot-water extract of the second extraction step with an alcohol or an aqueous alcohol solution as a solvent. The first extraction step, the extraction residue, the hot-water extraction, the precipitation and the alcohol or aqueous alcohol solution are the same as described above.

Hereinafter, the present disclosure will be described in detail through examples and test examples. However, the following examples and test examples are for illustrative purposes only and the scope of the present disclosure is not limited by them.

Examples Preparation of Green Tea Extract 500 kg of green tea powder prepared by pulverizing dried green tea leaves was extracted at 70° C. after adding 10,000 L of 70% (v/v) ethanol. The extract was concentrated to ⅕ of initial volume and then filtered first. A portion of the first filtrate was dried to obtain a 35% green tea extract, which was used as Comparative Example. An extraction residue with chlorophylls and low-molecular-weight polyphenols removed was obtained by centrifuging the remaining first filtrate.

The extraction residue with chlorophylls and low-molecular-weight polyphenols removed was subjected to hot-water extraction at 90° C. for 3 hours after adding 50,000 L of water. Then, a portion of the hot-water extract was concentrated under reduced pressure to ⅕ of initial volume, and then dried at 120° C. to obtain 15,000 g of a green tea extract (Example 1).

After adding 500 L of 95% (v/v) ethanol to the remaining hot-water extract, ethanol precipitation was conducted by centrifuging. Then, the precipitate was dried at 120° C. to obtain 70,000 g of a green tea extract (Example 2).

Test Example 1 Analysis of Ingredients of Green Tea Extract

The ingredients of the green tea extracts obtained above (Comparative Example, Example 1 and Example 2) were analyzed as described below.

Test Example 1-1 Analysis of Polysaccharide

50 mg of glucose was added to a 50-mL volumetric flask (1 mg/mL), and the stock solution was diluted with distilled water to prepare standard solutions of different concentrations. Then, a 0.1-0.5% aqueous solution of each of the green tea extracts (Comparative Example, Example 1 and Example 2) was dissolved sufficiently by stirring for at least 2 hours. After removing insoluble materials from the solution by centrifugation (8000 rpm, 30 minutes) or by using a vacuum filter (20-25 μm), the solution was pretreated after transferring to a dialysis tube. Then, after adding the pretreated green tea extract to a dialysis tube and sealing the ends of the tube, dialysis was performed for 24 hours after immersing the tube in distilled water. Then, the total volume of the dialyzed solution was measured. Distilled water was exchanged during the dialysis. A portion of the solution was used as a test solution for measurement of polysaccharide content. After adding 200 μL of each of the standard solution and the test solution to a test tube and mixing with 1 mL of a 5% phenol solution, 5 mL of concentrated sulfuric acid was added to the mixture solution. After conducting reaction for 20 minutes, absorbance was measured at 490 nm. Distilled water was subjected to the same operation as a control solution instead of the test solution. From the absorbance measured at 490 nm, polysaccharide content (mg/g) was calculated according to Equation 1.

Polysaccharide content (mg/g)=$C \times (a \times b)/S \times 1/1,000$    [Equation 1]

C: sample concentration (μg/mL) determined from calibration curve
  a: total volume (mL) of dialyzed test solution
  b: dilution factor
  S: sample amount (g)
  1/1,000: conversion factor

Test Example 1-2 Analysis of Catechin

For catechin analysis, catechins were extracted sufficiently from the green tea extracts (Comparative Example, Example 1 and Example 2) by treating with methanol and sonication and then quantitative analysis was conducted by liquid chromatography-UV spectroscopy at the maximum absorption wavelength of 280 nm. Reference materials and analysis procedures used for the catechin analysis are as follows.

(Reference material 1)

(-)-Epigallocatechin (EGC)
Molecular formula: $C_{15}H_{14}O_7$,
molecular weight: 306.27
CAS No.: 970-74-1

(Reference material 2)

(-)-Epigallocatechin (EGCG)
Molecular formula: $C_{22}H_{18}O_{11}$,
molecular weight: 458.37
CAS No.: 987-51-5

(Reference material 3)

(-)-Epicatechin (EC)
Molecular formula: $C_{15}H_{14}O_6$,
molecular weight: 290.27
CAS No.: 490-46-0

(Reference material 4)

(-)-Epigallocatechin (ECG)
Molecular formula: $C_{22}H_{18}O_{10}$,
molecular weight: 442.37
CAS No.: 1257-08-5

10 mg of each of the four reference materials was added to a 10-mL volumetric flask and methanol was filled up to the calibration mark. The diluted solution was used to create a calibration curve. Then, after adding each of the green tea extracts of the examples to a 100-mL volumetric flask in an amount such that the sum of the four reference material epigallocatechin (EGC), epigallocatechin gallate (EGCG), epicatechin (EC) and epicatechin gallate (ECG) was 20-80 mg, and conducting ultrasonic extraction by adding methanol, methanol was filled up to the calibration mark and the resultant was filtered through a 0.45-μm membrane filter. Then, HPLC analysis was conducted under the conditions of Tables 1 and 2.

TABLE 1

| HPLC condition | |
|---|---|
| Injection volume | 20 μL |
| Detection wavelength | 280 nm |
| Column temperature | 40° C. |
| Mobile phase | A: 0.1% acetic acid solution, B: 100% acetonitrile |
| Flow rate | 10 mL/min |

TABLE 2

| Mobile phase condition | | |
|---|---|---|
| Time (min) | Solution A (%) | Solution B (%) |
| 0 | 95 | 5 |
| 20 | 75 | 25 |
| 21 | 0 | 100 |
| 35 | 0 | 100 |
| 36 | 95 | 5 |
| 50 | 95 | 5 |

The contents of the four catechins and total catechin content in the green tea extracts (Comparative Example, Example 1 and Example 2) were calculated according to Equation 2 and Equation 3.

$$\text{Content (mg/g) of each catechin} = C \times (a \times b)/S \times 1/1{,}000 \quad \text{[Equation 2]}$$

C: concentration (μg/mL) of each catechin in test solution
a: total volume (mL) of test solution
b: dilution factor
S: sample amount (g)
1/1,000: conversion factor $$\text{Total catechin content (mg/g)} = \text{EGC (mg/g)} + \text{EGCG (mg/g)} + \text{EC (mg/g)} + \text{ECG (mg/g)} \quad \text{[Equation 3]}$$

Test Example 1-3 Analysis of Dietary Fiber

The dietary fibers of the green tea extracts (Comparative Example, Example 1 and Example 2) were analyzed by the enzymatic-gravimetric method using a phosphate buffer, which is applied to foods containing resistant maltodextrin (RMD), by identifying water-soluble dietary fiber (HMWSDF) precipitated by ethanol, such as high-molecular-weight resistant maltodextrin, and identifying water-soluble dietary fiber (LMWSDF) dissolved in ethanol, such as low-molecular-weight resistant maltodextrin, after concentration by desalting, by liquid chromatography. Total dietary fiber was calculated as the sum of the water-insoluble dietary fiber (IDF), HMWSDF and LMWSDF identified by liquid chromatography. That is to say, the content of the dietary fibers contained in the green tea extracts (Comparative Example, Example 1 and Example 2) was determined by summing the dietary fiber content of determined by the enzymatic-gravimetric method with the content of water-soluble dietary fibers dissolved in alcohol.

Test Example 1-4 Analysis of Monosaccharide and Disaccharide

Standard sugar solutions were prepared by dissolving standard sugars (fructose, glucose and sucrose) dried in a vacuum oven at 60° C. for 12 hours in distilled water. The concentration of the standard sugars for creating calibration curves was adjusted such that the peak area of the test solution could satisfy the linearity of each reference sugar. For the monosaccharide and disaccharide analysis, a mobile phase was prepared by mixing acetonitrile and distilled water at a volume ratio of 80:20. The mobile phase was used after filtering through a glass fiber filter (Whatman GF/F 0.7 μm or equivalent thereof) or a nylon 66 filter (Pall 0.45 μm or equivalent thereof) and degassing by sonication.

For preparation of test solutions, each of the green tea extracts (Comparative Example, Example 1 and Example 2) was homogenized and 5 g of the homogenized sample was precisely weighed into a 50-mL centrifugation tube and then dispersed with 25 mL of petroleum ether. After centrifuging at 2,000 rpm for about 10 minutes, the petroleum ether was removed cautiously such that the solid matter was not removed. After repeating this procedure, the petroleum ether was evaporated completely using nitrogen. For a sample identified to be free of fats, the defatting process was omitted. After adding 25 mL of distilled water or a 50% ethanol solution to each of the defatted green tea extracts, weight was recorded and then fructose, glucose and sucrose were extracted by heating in a water bath at 85° C. for 25 minutes. After cooling to room temperature, an extraction solvent was added to compensate for the weight loss. Then, a test solution was obtained by filtering the solution through a 0.45-μm nylon membrane filter. If the test solution was turbid, it was centrifuged at 2,000 rpm for 10 minutes. Liquid chromatography (LC) was conducted under the condition of Table 3.

TABLE 3

| | LC condition |
|---|---|
| Column | Length 300 mm, inner diameter 4 mm, μ-Bondapak carbohydrate column |
| Detector | Refractive index (RI) detector |
| Mobile phase | Acetonitrile:distilled water (80:20, w/w) |
| Flow rate | 1.0 mL/min |
| Column temperature | Room temperature |

After creating a calibration curve from the peak area or height obtained by injecting 10 μL of each of the test solution and the standard solution, the concentration (μg/mL) of fructose, glucose and sucrose in each test solution was determined. Then, the content (mg/100 g) of fructose, glucose and sucrose in the sample was calculated using Equation 4. The concentration range of the calibration curve was adjusted such that the linearity for the concentration of fructose, glucose and sucrose in the test solution could be satisfied.

$$\text{Sugar content (mg/100g)} = S \times (a \times b/\text{sample amount (g)}) \times (100/1000) \quad \text{[Equation 4]}$$

S: concentration (μg/mL) of sugar in test solution
a: total volume (mL) of test solution
b: dilution factor

Test Example 1-5 Analysis Result of Green Tea Extract Ingredients

The result of analyzing the ingredients of the green tea extracts (Comparative Example, Example 1 and Example 2) according to the methods of Test Examples 1-1 to 1-4 is shown in Table 4. In Table 4, the content of each ingredient is expressed as wt % based on the total weight of the green tea extract.

TABLE 4

| | | | | | (Unit: wt %) | |
|---|---|---|---|---|---|---|
| | Polysaccharide | Catechin | Dietary fiber | Glucose | Fructose | Sucrose |
| Comparative Example | 5.151 | 37 | 0.69 | 0.66 | 0.643 | 7.12 |
| Example 1 | 9.373 | 5.1 | 13.67 | 2.074 | 1.433 | 2.335 |
| Example 2 | 9.985 | 4 | 15.56 | 2.17 | 1.811 | 1.586 |

As seen from Table 4, Examples 1 and 2, which were obtained by hot-water extracting the extraction residue of green tea or precipitating the same with ethanol, contained about 1.8 times or more of polysaccharides, less than about 1/7 of catechins and about 20 times or more of dietary fibers as compared to Comparative Example, and contained glucose, fructose and sucrose, which are monosaccharides or disaccharides, in an amount less than 2/3 as compared to Comparative Example. Through this, it can be seen that Examples 1 and 2 contain more polysaccharides and dietary fibers and less catechins, monosaccharides and disaccharides as compared to Comparative Example.

Test Example 2 Inhibitory Effect Against Glucosidase Activity

In Test Example 1, it was confirmed that Examples 1 and 2, which were obtained from hot-water extraction or ethanol precipitation of the extraction residue of green tea, exhibited different contents of ingredients as compared to Comparative Example. Thus, the degree of inhibition of glucosidase activity was measured as follows in order to investigate whether the green tea extracts of Examples 1 and 2 exhibit blood glucose-lowering effect by inhibiting carbohydrate digestion.

1 μL of 20 mU/mL α-glucosidase was mixed with 97 μL of the green tea extracts of Examples 1 and 2 dissolved in a 0.1 M calcium phosphate buffer to concentrations of 0.25 ppm, 0.5 ppm, 1 ppm or 2 ppm. 30 minutes later, 2 μL of a substrate solution (α-NPG (p-nitrophenyl-α-D-glucopyranoside)) was added. After conducting reaction for 15 minutes, the reaction was stopped by adding sodium carbonate. Then, absorbance was measured at 405 nm and the inhibition of α-glucosidase activity was calculated according to Equation 5. The result is shown in Table 5.

$$\text{Inhibition (\%) of α-glucosidase activity} = (\text{α-glucosidase activity of control group} - \text{α-glucosidase activity of green tea extract of Example})/\text{α-glucosidase activity of control group} \times 100 \quad \text{[Equation 5]}$$

The α-glucosidase activity of the control group is the activity measured when only the substrate solution was reacted with α-glucosidase.

TABLE 5

| | Inhibition (%) of α-glucosidase activity | |
|---|---|---|
| | Example 1 | Example 2 |
| 0.25 ppm | 24.7991 | 26.9314 |
| 0.5 ppm | 36.8820 | 38.2571 |
| 1 ppm | 42.5525 | 30.0062 |
| 2 ppm | 74.4592 | 54.9289 |

As seen from Table 5, the green tea extracts of Examples 1 and 2 were effective in inhibiting the α-glucosidase activity in a concentration-dependent manner. Therefore, it can be seen that a green tea extract containing 7 wt % or more of a polysaccharide, less than 20 wt % of catechin, 10 wt % or more of a dietary fiber, and less than 7 wt % of a monosaccharide and a disaccharide based on the total weight of the green tea extract may have an effect of lowering blood glucose by inhibiting α-glucosidase activity.

Test Example 3 Inhibitory Effect Against Amylase Activity

As in Test Example 2, the degree of inhibition of amylase activity was measured as follows in order to investigate whether the green tea extracts of Examples 1 and 2 exhibit blood glucose-lowering effect by inhibiting carbohydrate digestion.

160 μL of 4 mU/mL α-amylase was mixed with 20 μL of each of a guava extract known as a substance regulating blood glucose or the green tea extracts of Examples 1 and 2 dissolved in a 20 mM sodium phosphate buffer containing 6.7 mM sodium chloride to concentrations of 250 ppm, 500 ppm or 1000 ppm. 10 minutes later, 200 μL of starch was added. After conducting reaction for 10 minutes, 200 μL of a color-developing reagent containing Rochelle salt (potassium sodium tartrate tetrahydrate) and 3,5-dinitrosalicylic acid was added and the mixture was heated at 95° C. 5 minutes later, after cooling the heated solution and adding 580 μL of distilled water, absorbance was measured at 540 nm and the inhibition of α-amylase activity was calculated according to Equation 6. The result is shown in Table 6 and FIG. 1.

Figure 1:
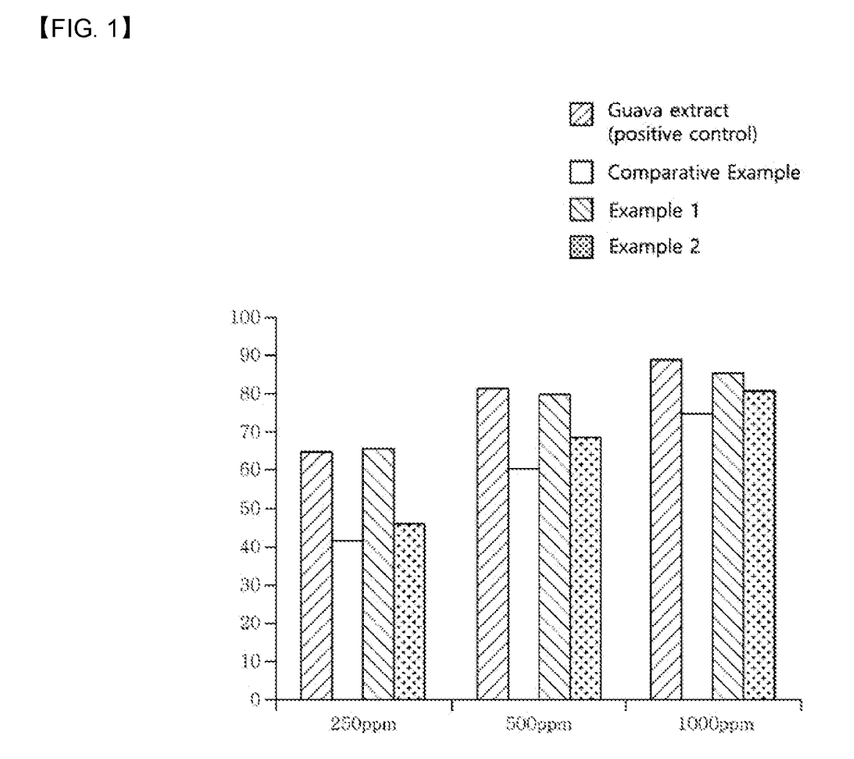
FIG. 1 shows the inhibition of α-amylase activity by guava extract as a positive control group and green tea extracts of Comparative Example and Examples 1 and 2 as green tea extracts prepared according to an exemplary embodiment of the present disclosure.
Figure 2:
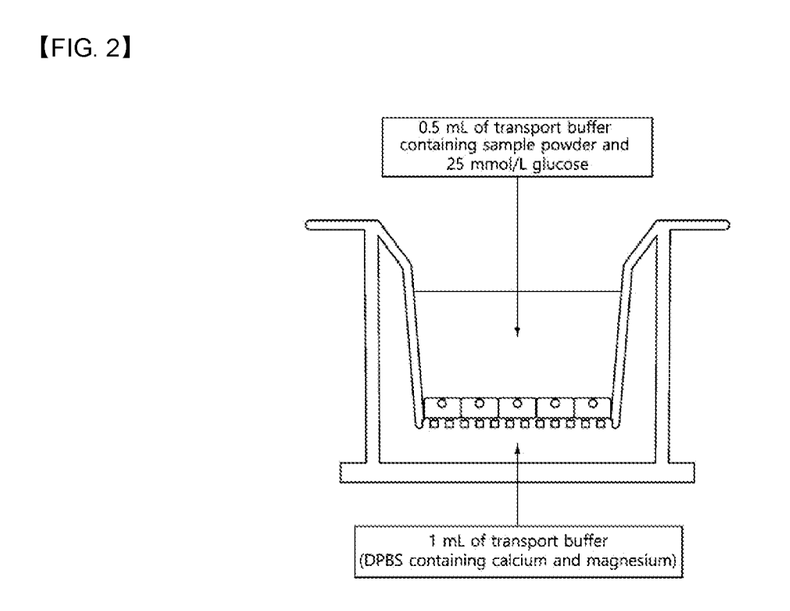
FIG. 2 illustrates a method for investigating glucose uptake in small intestine cells by using transepithelial electrical resistance (TEER).

Inhibition (%) of α-amylase activity=(α-amylase activity of control group–α-glucosidase activity of green tea extract of Example)/α-amylase activity of control group×100  [Equation 6]

The α-amylase activity of the control group is the activity measured when only the substrate solution was reacted with α-amylase.

TABLE 6

Inhibition (%) of α-amylase activity

|  | Guava extract | Comparative Example | Example 1 | Example 2 |
|---|---|---|---|---|
| 250 ppm | 64.9931 | 41.8257 | 65.88404 | 46.2666 |
| 500 ppm | 81.6095 | 60.3674 | 80.1551 | 68.6555 |
| 1000 ppm | 88.9393 | 74.7218 | 85.4304 | 80.7232 |

As seen from Table 6 and FIG. 1, the green tea extracts of Examples 1 and 2 were effective in inhibiting the α-amylase activity in a concentration-dependent manner, and the degree was similar to that of the guava extract as the positive control group. In addition, Examples 1 and 2 showed higher α-amylase activity than Comparative Example. Therefore, it can be seen that a green tea extract containing 7 wt % or more of a polysaccharide, less than 20 wt % of catechin, 10 wt % or more of a dietary fiber, and less than 7 wt % of a monosaccharide and a disaccharide based on the total weight of the green tea extract may have an effect of lowering blood glucose by inhibiting α-amylase activity.

Test Example 4 Inhibitory Effect Against Glucose Uptake in Small Intestinal Epithelial Cells In order to investigate the effect of the green tea extracts of Examples 1 and 2 on the inhibition of glucose uptake in the small intestine, glucose uptake assay was conducted for small intestine cells (Caco-2 cells) using a 24-well insert (Cat #37024, sterile, SPL).

Specifically, Caco-2 cells were plated on a 24-well insert at $6 \times 10^4$ cells/well and then cultured for 2 weeks until 100% confluence under an environment similar to that of the human small intestine (5% $CO_2$, 37° C.). The cells were washed with PBS (phosphate-buffered saline) and the DMEM (Dulbecco's modified Eagle's medium) was replaced at 3- to 5-day intervals. The permeability of the small intestine cells was evaluated by measuring transepithelial electrical resistance (TEER) and the cells with TEER of 100 $\Omega/cm^2$ or higher were used.

Guava extract known to have blood glucose-regulating effect was used as a positive control group. Before treating the Caco-2 cells with the three green tea extracts (Comparative Example, Examples 1 and 2), they were washed twice with a transport buffer. 0.5 mL of a mixture of 250 μg/mL of each of the positive control group, Comparative Example, Examples 1 and 2 with 25 mmol/L glucose was treated onto the apical layer of the 24-well insert (hereinafter, referred to as 'glucose-treated groups'). In order to investigate the difference in glucose uptake, separately from the glucose-treated groups, 0.5 mL of 250 μg/mL of each of the positive control group, Comparative Example, Examples 1 and 2 without being mixed with glucose was treated onto the apical layer of the 24-well insert (hereinafter, referred to as 'non-glucose-treated groups'). The concentrations of the substances treated to the glucose-treated groups and the non-glucose-treated groups are described in Table 7. The glucose-treated groups and the non-glucose-treated groups were incubated under the condition of 5% $CO_2$ and 37° C. for 1 hour.

TABLE 7

|  | Glucose-treated groups | Non-glucose-treated group |
|---|---|---|
| Glucose | 25 mmol/L | — |
| Guava extract (positive control) | 250 μg/mL | 250 μg/mL |
| Comparative Example | 250 μg/mL | 250 μg/mL |
| Example 1 | 250 μg/mL | 250 μg/mL |
| Example 2 | 250 μg/mL | 250 μg/mL |

The content of glucose absorbed by the small intestine cells was measured using a LabAssay glucose kit (mutarotase-GOD method, Wako). 300 μL of a chromogenic reagent containing a glucose-degrading enzymes and 2 μL of the glucose-treated group or the non-glucose-treated group were mixed well in a 96-well plate. After conducting reaction at 37° C. for 5 minutes, glucose content was determined by measuring absorbance at 505 nm and glucose uptake inhibition was calculated by Equation 7. The result is shown in Table 8 and FIG. 3. The standard curve for glucose was created after measurement at 1, 5, 10, 25, 50 and 100 mmol/L.

Figure 3:
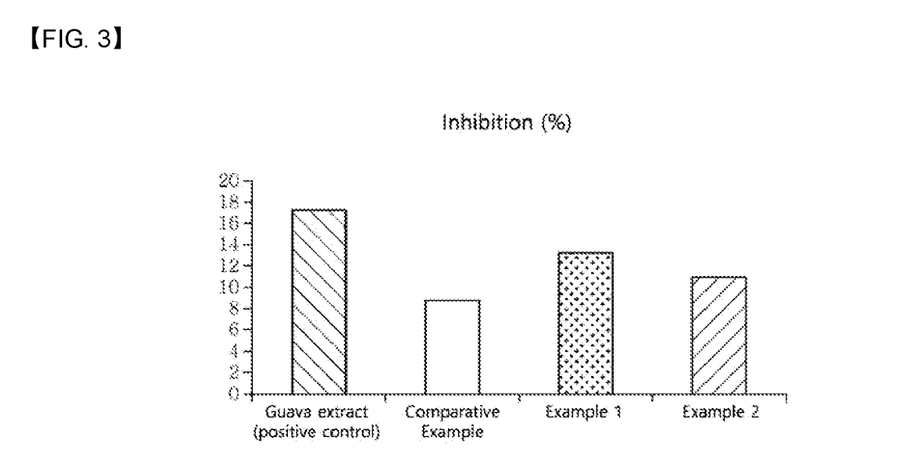
FIG. 3 shows the inhibition of glucose uptake in small intestine cells by guava extract as a positive control group and green tea extracts of Comparative Example and Examples 1 and 2 as green tea extracts prepared according to an exemplary embodiment of the present disclosure.

Inhibition (%) of glucose uptake=(sugar content of non-glucose-treated group–sugar content of glucose-treated group)/glucose content of glucose-treated group×100  [Equation 7]

TABLE 8

Inhibition of glucose uptake in small intestine cells

|  | Guava extract | Comparative Example | Example 1 | Example 2 |
|---|---|---|---|---|
| Inhibition (%) | 17.262 | 8.825 | 13.286 | 10.965 |

As seen from Table 8 and FIG. 3, the green tea extracts of Examples 1 and 2 prepared according to the present disclosure exhibited an effect of inhibiting glucose uptake in small intestine cells comparably to the positive control group (guava extract) and showed superior effect of inhibiting glucose uptake as compared to the green tea extract of Comparative Example.

Taken together with the effect of inhibiting the activity of carbohydrate-digesting enzymes (α-glucosidase and α-amylase) demonstrated in Test Examples 2 and 3, it can be seen that, although the green tea extract of Comparative Example has an effect of inhibiting carbohydrate digestion by inhibiting the activity of carbohydrate-digesting enzymes, a sufficient blood glucose-lowering effect cannot be expected because the effect of inhibiting the absorption of glucose existing in the small intestine into small intestine cells is insignificant. In contrast, it was confirmed that the green tea extracts of Examples 1 and 2 of the present disclosure exhibit superior blood glucose-lowering effect by effectively inhibiting carbohydrate digestion and effectively inhibiting glucose uptake by small intestine cells. Therefore, it can be seen that a green tea extract containing 7 wt % or more of a polysaccharide, less than 20 wt % of catechin, 10 wt % or more of a dietary fiber and less than 7 wt % of a monosaccharide and a disaccharide based on the total weight of the green tea extract has an effect of lowering blood glucose by inhibiting carbohydrate digestion and inhibiting glucose uptake in small intestine cells.

Hereinafter, the present disclosure will be described in detail through formulation examples. However, the following formulation examples are for illustrative purposes only and the scope of the present disclosure is not limited by them.

Formulation Example 1 Preparation of Powder Formulation

| Green tea extract of Example 1 or 2 | 2 g |
|---|---|
| Lactose | 1 g |

A powder formulation was prepared by mixing the above-described ingredients and filling the mixture in a sealed pouch.

Formulation Example 2 Preparation of Tablet

| Green tea extract of Example 1 or 2 | 100 mg |
|---|---|
| Cornstarch | 100 mg |
| Lactose | 100 mg |
| Magnesium stearate | 2 mg |

A tablet was prepared according to a common method after mixing the above-described ingredients.

Formulation Example 3 Preparation of Capsule

| Green tea extract of Example 1 or 2 | 100 mg |
|---|---|
| Cornstarch | 100 mg |
| Lactose | 100 mg |
| Magnesium stearate | 2 mg |

After mixing the above-described ingredients, a capsule was prepared according to a common method by filling the mixture in a gelatin capsule.

Formulation Example 4 Preparation of Pill

| Green tea extract of Example 1 or 2 | 1 g |
|---|---|
| Lactose | 1.5 g |
| Glycerin | 1 g |
| Xylitol | 0.5 g |

After mixing the above-described ingredients, a pill was prepared such that each pill weighs 4 g.

Formulation Example 5 Preparation of Granule

| Green tea extract of Example 1 or 2 | 150 g |
|---|---|
| Soybean extract | 50 mg |
| Glucose | 200 mg |
| Starch | 600 mg |

After mixing the above-described ingredients and adding 100 mg of 30% ethanol, a granule formed by drying at 60° C. was filled in a pouch.

Formulation Example 6 Preparation of Drink

| Green tea extract of Example 1 or 2 | 50 mg |
|---|---|
| Glucose | 10 g |
| Citric acid | 0.6 g |
| Oligosaccharide syrup | 25 g |

After mixing the above-described ingredients and adding 300 mL of purified water, 200 mL of the mixture was filled per bottle and then sterilized at 130° C. for 4-5 seconds to obtain a drink.

Formulation Example 7 Preparation of Caramel

| Green tea extract of Example 1 or 2 | 50 mg |
|---|---|
| Corn syrup | 1.8 g |
| Skim milk | 0.5 g |
| Soybean lecithin | 0.5 g |
| Butter | 0.6 g |
| Hydrogenated vegetable oil | 0.4 g |
| Sugar | 1.4 g |
| Margarine | 0.58 g |
| Table salt | 20 mg |

The above-described ingredients were mixed and then formed into a caramel.

The invention claimed is:

1. A method for regulating blood glucose, the method comprising:
administering an effective amount of a composition comprising a green tea extract comprising 7 wt % or more of a polysaccharide, less than 20 wt % of catechin and 10 wt % or more of a dietary fiber based on the total weight of the green tea extract to a subject in need of blood glucose regulation.

2. The method according to claim 1, wherein the green tea extract further comprises less than 7 wt % of a monosaccharide and a disaccharide based on the total weight of the green tea extract.

3. The method according to claim 1, wherein the green tea extract comprises 9 wt % or more of a polysaccharide based on the total weight of the green tea extract.

4. The method according to claim 1, wherein the green tea extract comprises 13 wt % or more of a dietary fiber based on the total weight of the green tea extract.

5. The method according to claim 1, wherein the composition lowers blood glucose.

6. The method according to claim 1, wherein the composition inhibits carbohydrate digestion and glucose uptake in small intestine cells.

7. The method according to claim 6, wherein the inhibition of carbohydrate digestion is achieved by inhibiting the activity of amylase or glucosidase.

8. The method according to claim 1, wherein the green tea extract is a hot-water extract obtained by hot-water extracting an extraction residue of an extract obtained by adding an alcohol or an aqueous alcohol solution to green tea as a first solvent.

9. The method according to claim 8, wherein the green tea extract is an alcohol or aqueous alcohol solution precipitate of the hot-water extract.

10. The method according to claim 1, wherein the composition is a pharmaceutical composition.

11. The method according to claim 1, wherein the composition is a food composition.

\* \* \* \* \*